United States Patent [19]
Hirsch

[11] Patent Number: 5,492,934
[45] Date of Patent: Feb. 20, 1996

[54] CHEMOSENSORY OLFACTORY ASSAY FOR SOMATIZATION DISORDERS

[76] Inventor: Alan R. Hirsch, 180 E. Pearson, #4702, Chicago, Ill. 60611

[21] Appl. No.: 316,520

[22] Filed: Sep. 30, 1994

Related U.S. Application Data

[62] Division of Ser. No. 229,059, Apr. 18, 1994, Pat. No. 5,380,765, which is a continuation of Ser. No. 954,882, Sep. 30, 1992, abandoned.

[51] Int. Cl.$^6$ .................................................. A61K 31/045
[52] U.S. Cl. ....................................................... 514/730
[58] Field of Search ............................................. 514/730

[56] References Cited

PUBLICATIONS

*The Accusens T™ Taste Function Kit Directions for Use*, published by Westport Pharmaceuticals Inc., Westport, CT, 1982.
J. Amoore et al., "Practical Test Kits for Quantitatively Evaluating the Sense of Smell", *Rhinology*, 21:49 (1983).
J. Amoore et al., "Odor as an Aid to Chemical Safety: Odor Thresholds Compared with Threshold Limit Values and Volatilities for 214 Industrial Chemicals in Air and Water Dilution", *J. Applied Toxicology, 3:272 (1983)*.
Amsterdam et al., "Taste and Smell Perception in Depression", *Biol. Psychiatry*, 22:1477 (1987).
Doty et al., *The Smell Identification Test™ Administration Manual*, published by Sensonics, Inc. (1983).
Doty et al., "Development of the University of Pennsylvania Smell Identification Test: A Standardized Microencapsulated Test of Olfactory Function", *Physiology and Behavior*, 32:489 (1984).
Doty et al., "smell Identification Ability: Changes with Age", *Science*, 226:1441 (1984).
Doty et al., "Internal Consistency and Short–Term Test–Retest Reliability of the University of Pennsylvania Smell Identification Test", *Chemical senses*, 10:297 (1985).
Harrison et al., "Olfaction and Psychiatry", *Brit. J. Psychiatry*, 155:822 (1989).
Hirsch et al., "Post–Traumatic Dysosmia: Central vs. Peripheral", *84th Annual Scientific Assembly of the Southern Medical Association*, at page 2S–34 (1990).
Hirsch et al., "Post–Traumatic Dysosmia: Central vs. Peripheral", *The 13th Annual Meeting of the Association for Chemoreception Sciences* at page 225 (1991).
Hirsch et al., "Co–morbidity of Psychiatric and Chemosensory Disorders", *Chemical Senses*, vol. 16, Abstract No. 92 (1991).
Jesberger et al., "Brain Output Disregulation Induced by Olfactory Bulbectomy: An Approximation in the Rat of the Major Depressive Disorder in Humans?", *Intern. J. Neuroscience*, 38:241 (1988).
"Administration, Scoring and Coding", *Psychological Assessment with the MMPI*, A. Friedman et al., editor, Lawrence Erlbaum Associates, Hillsdale, NJ, publishers, at pp. 40–53 (1989).
"Interpretation of MMPI Clinical Skills", *Psychological Assessment with the MMPI*, A. Friedman et al., editor, Lawrence Erlbaum Associates, Hillsdale, NJ publishers at pp. 150–198 (1989).
Schiffmann et al., "Taste and Smell in Disease", *New Eng. J. Med.*, 308:1275 (1983).

*Primary Examiner*—Raymond Henley, III
*Assistant Examiner*—William R. A. Jarvis
*Attorney, Agent, or Firm*—Merchant, Gould, Smith Edell, Welter & Schmidt

[57] ABSTRACT

The invention provides a method for diagnosing a somatization disorder in a patient. The method involves administering to the patient a plurality of concentrations of the chemosensory agent 3-methyl-5-phenyl-3-pentanol, identifying at least a 5 decismel change in the threshold amount of the chemosensory agent detected by the patient, and correlating the change in detection of the chemosensory agent with at least one psychiatric disorder.

2 Claims, No Drawings

CHEMOSENSORY OLFACTORY ASSAY FOR SOMATIZATION DISORDERS

This is a division of application Ser. No. 08/229,059, filed Apr. 18, 1994, now U.S. Pat. No. 5,380,765, which is a continuation of application Ser. No. 07/954,882, filed Sep. 30, 1992, now abandoned, which application is incorporated herein by reference.

BACKGROUND OF THE INVENTION

The ability to smell and, in part, the ability to taste is regulated by the olfactory nerve system. The olfactory nerve system is complex and interconnected with several systems in the brain. Olfactory receptors located in the nose are specialized bipolar neurons with cilia protruding into the mucous covering the epithelium. The axons of the bipolar neurons are packed into bundles that form connections in the olfactory bulb in the brain. The olfactory bulbs contain a rich supply of neurotransmitters and neuromodulators. Neuromodulators include thyrotropin releasing hormone, substance P, enkephalin, dopamine, glutamate, and aspartate. The neurotransmitters include serotonin, acetylcholine and noradrenaline which are delivered to the bulbs from cell bodies in other brain regions and are formed within the bulbs in the terminal projections only. Central olfactory projections from the bulb interconnect the bulb to other areas of the brain, including the hippocampus, the hypothalamus, and the pyriform lobe.

There is an anatomical and biochemical connection between the olfactory system and the limbic system in the brain. The limbic system includes the hippocampus and amygdala region, and is known as the emotional center of the brain. The limbic regions have many synaptic contacts with olfactory bulbs. Many of the limbic structures and the olfactory bulbs are reciprocally interconnected in loop pathways that may be involved in the regulation of brain emotional output.

There are several known disorders of taste and smell which affect the function of the olfactory system and which present major problems for the patient. Chemosensory dysfunctions are usually described by the following terms: ageusia (absence of taste), hypogeusia, (diminished sensitivity of taste), dysgeusia (distortion of normal taste), anosmia (absence of smell), hyposmia (diminished sense of smell), and dysosmia (distortion of normal smell). These disorders cause modification of food choices and dietary habits, alter digestion, and the ability to detect noxious gases and poisons. Overall, chemosensory disorders are chronic problems that can reduce enjoyment and quality of life.

It is also known that neurological disorders involving damage to the brain can also include a chemosensory dysfunction. For example, patients suffering from Alzheimer's disease show a marked impairment in smell identification which may be associated with senile plaques, neurofibrillary tangles, and reduced cholinergic activity in the olfactory bulb.

SUMMARY OF THE INVENTION

The invention provides a method for diagnosing psychiatric disorder in a patient by administering a plurality of concentrations of a chemosensory agent, identifying at least a 5 decismel change in the threshold amount of at least one chemosensory agent detected by the patient and correlating that change with a diagnosis of at least one psychiatric disorder. Patients, particularly those presenting with a chemosensory dysfunction, can be tested with various olfactory or gustatory chemosensory agents and the threshold level of detection of those agents by the patient identified. Once identified, the threshold level of detection by the patient of at least one chemosensory agent is compared with the normal threshold amount and at least a 5 decismel change in the threshold amount detected by the patient can indicate a chemosensory and a psychiatric disorder. This invention is based on my discovery that the change in the threshold level of detection of a particular chemosensory agent correlates with a psychiatric disorder which has been confirmed in independent behavioral diagnosis. In a preferred version, the chemosensory agent is PE-phenol and the psychiatric disorder is depression.

The invention also provides for a kit for diagnosing a psychiatric disorder including: at least one chemosensory agent present in increasing concentrations ranging from sub-threshold to suprathreshold amounts; optionally, a chart indicating the expected threshold amounts for each of the chemosensory agents for each age group and sex of patients; and a chart of psychiatric disorders wherein the chart correlates a psychiatric disorder with at least a 5 decismel change in the threshold amount of the chemosensory agent detected by the patient. The kit preferably contains at least 10 different concentrations of one or more chemosensory agents and a chart correlating detection level of several chemosensory agents with different psychiatric disorders as shown in Table V.

DETAILED DESCRIPTION OF THE INVENTION

The invention provides a method of diagnosing psychiatric disorders in a human patient who has a chemosensory dysfunction or disorder. Patients with a chemosensory dysfunction have an alteration in the ability to taste or smell at least one chemosensory agent. A chemosensory agent is a compound that can be detected by a human's sense of smell or taste. Chemosensory dysfunctions or disorders are usually described by the following terms: ageusia (absence of taste), hypogeusia, (diminished sensitivity of taste), dysgeusia (distortion of normal taste), anosmia (absence of smell), hyposmia (diminished sense of smell), and dysosmia (distortion of normal smell). Using the method of the invention, a chemosensory dysfunction in the detection of at least one chemosensory agent correlates with and can be used to confirm a known psychiatric diagnosis.

A patient is evaluated for a chemosensory dysfunction using standard chemosensory assays known to those of skill in the art. The patient's ability to detect the type and threshold amount of a chemosensory agent by the sense of taste or smell is measured. The preferred chemosensory assays include the Smell Identification Test™, the Accusens T™ Taste Test, and unilateral threshold tests. The unilateral threshold test can be conducted by standard methods and provides for olfactory testing with any number of chemosensory agents. The standards for unilateral threshold testing in decismels, including the threshold concentrations for the chemosensory agents, can be obtained from OlfactoLabs, El Cerrito, Calif.

The chemosensory agent can be administered to the patient by smelling or tasting. The ability to detect the chemosensory agent in the right and left nostrils is tested separately. Preferably, different concentrations of the chemosensory agent are randomly given to the patient along with samples that do not contain the chemosensory agent.

Preferably, the patient correctly identifies the chemosensory agent at a particular concentration at least three times before the patient is scored as having correctly detected the chemosensory agent at that concentration. The threshold level of detection is the minimum concentration of the chemosensory agent detected by the patient.

Suitable examples of olfactory chemosensory agents include trichloroethene, 1,2-dichloropropane, isobutyl isobutyrate, naphthalene, pyridine, 4-ethylphenol, 3-methyl-5-phenyl-3-pentanol (hereinafter "phenylethyl methylethyl carbinol" or "carbinol"), tetrahydrothiophene, isovaleric acid, trimethylamine, L-carvone, pentadecalactone, 1-pyrroline, 1,8-cineole, isobutyraldehyde, 16-androsten-3-one, thiophane, PE-phenol (p-ethylphenol), CA-phenone ($\alpha$-chloro-acetophenone), as well as the chemosensory agents in the Smell Identification Test™. Suitable gustatory chemosensory agents include salt (NaCl), sucrose, hydrochloric acid (HCl), urea, and phenylthiocarbamide (PTC). The preferred chemosensory agent is PE-phenol.

The patient's threshold level for detecting a chemosensory agent is identified and compared to the known threshold values for the same sex and age group. If the test samples containing a chemosensory agent are obtained from a commercial source, such as OlfactoLabs, El Cerrito, Calif., the samples are already calibrated in decismels and no conversion from absolute threshold concentration to decismels is necessary. Alternatively, the normal threshold concentration can be determined by administering the same concentrations of the chemosensory agent to a control group of at least 25 humans, who do not have a chemosensory dysfunction, and calculating the mean threshold concentration detected by the group of 25 individuals. Another alternative is to refer to the known threshold value for the chemosensory agent that has been established previously and published by J. Amoore et al., *J. Appl. Toxicology*, 3:272 (1983). A range of about −50 to +60 decismels is administered to the patient. A change of at least 5 decismels (about a 2-fold concentration change) from the normal or expected value is considered significant and indicative of a chemosensory dysfunction.

Odor thresholds are expressed on the decismel scale. The decismel scale is constructed by setting the mean threshold concentration of a chemosensory agent detected by the control group of 20 year olds at the 0 value. A decismel is calculated by dividing the concentration of the chemosensory agent detected by the patient by the normal threshold concentration (using the published value or empirically determining the value) and then taking the logarithm of the quotient. The logarithm of the quotient is then multiplied by 20 to obtain the decismel value. Decismel values can be positive or negative. A positive decismel value indicates the patient is less sensitive to the chemosensory agent, i.e. has a higher threshold detection concentration. A negative decismel value indicates that the patient is more sensitive to the compound, i.e. has a lower threshold detection concentration. An increase in the threshold concentration value over the mean threshold concentration value of 2-fold, corresponds to 6 decismels (or ds).

The suggested thresholds for hyposmia are 30 ds and functional anosmia at 54 ds. A change of at least 5 ds from the normal or expected value was considered a significant change in the threshold level of detection of the compound. Suitable corrections can also be made for the age of the patient. The threshold increase with aging is about 6 ds between ages 20 and 40, and another 6 ds between 40 and 60.

The change in detection of sensitivity to at least one chemosensory agent is correlated with a known psychiatric diagnosis by reference to a chart, such as that provided in Table V. A change in detection of a chemosensory agent correlates with a particular psychiatric disorder. For example, at least a 5 ds decrease in threshold detection level of PE-phenol in the left nostril correlates with depression. The more severe the depression, the greater the decrease in the threshold detection level of PE-phenol.

Other psychiatric diagnoses can also correlate with a chemosensory dysfunction as follows: a decrease in the threshold detection level of PE-phenol with depression; an increase in the threshold detection level of thiophane detected in the right nostril and a decrease in the left nostril with obsessive-compulsive personality disorder; an increase in the threshold detection level for CA-phenone, pyridine, salt, and sucrose with a dependent personality disorder; a decrease in the threshold detection level of salt and sucrose with anti-social personality disorder; an increase in the threshold detection level detected of CA-phenone with atypical personality disorder; an increase in the threshold detection levels detected for pyridine and CA-phenone with a passive-aggressive personality disorder; an increase in the threshold detection level for carbinol with a somatization disorder; and an increase in the threshold detection level of CA-phenone and thiophane correlates with schizoid personality disorder.

Optionally, a psychiatric diagnosis of the patient can be confirmed by methods known to those of skill in the art. Those methods can include a psychiatric interview, or administration of one or more written psychological tests, or a combination of both. Suitable examples of written psychological tests include the Minnesota Multiphasic Personality Inventory I and II (MMPI-I and MMPI-II), the Millon Clinical Multiaxial Inventory II™ (MCMI-II), the Beck Depression Inventory™. The tests are administered and analyzed by methods known to those of skill in the art. Patients having a chemosensory dysfunction in the detection of at least one chemosensory agent can also be given at least one written psychological test to confirm the psychiatric diagnosis which can then be analyzed by standard methodologies known to those of skill in the art.

Alternatively, the chemosensory assay can be used to confirm a suspected psychiatric disorder. The suspected psychiatric diagnosis can be suggested from the results of a psychiatric interview or by administration of one or more written psychological tests, or both. The chemosensory assay can be administered to a patient suspected of having a psychiatric disorder and used to confirm the psychiatric disorder.

In the preferred method, the threshold detection level of PE-phenol in a patient is determined in both the left and right nostrils separately. At least 10 separate samples with different concentrations of PE-phenol ranging from subthreshold to suprathreshold (i.e., −50 decismels to +60 decismels) are intermixed with samples containing water only. The patient is asked to smell a water sample, followed by a PE-phenol sample at a particular concentration, or in reverse order. The exposure with the same concentration of PE-phenol is repeated at least three times. The patient preferably correctly identifies a sample of the PE-phenol at least three times before a score indicating detection is marked for that concentration. The minimum concentration detected by the patient is identified as the threshold level and, if necessary, this level can be converted to decismels using the normal known or expected threshold value for PE-phenol. A decrease of at least 5 ds in the threshold detection level is correlated with depression, and the greater the decrease in the threshold detection levels of the patient, the more severe the depression. Optionally, the diagnosis of depression can be confirmed by administering one psychological test, preferably the Beck Depression Inventory™.

The invention is also directed to a kit for diagnosing a psychiatric disorder. The kit includes at least one chemosensory agent present in a variety of concentrations ranging from sub-threshold to suprathreshold amounts for that chemosensory agent. The normal or expected threshold concentration can be a known value published by Amoore et al., cited supra., or can be determined empirically by testing a group of normal individuals with a plurality of concentrations of the chemosensory agent and calculating the means threshold concentration. Alternatively, the concentrations of the chemosensory agent can be supplied already converted to decismels, as described previously. A sub-threshold amount is a concentration of the chemosensory agent below the normal or expected threshold concentration for that chemosensory agent. A suprathreshold amount is a concentration of the chemosensory agent greater than the threshold amount. The kit preferably contains about 10–64 different concentrations of the chemosensory agent ranging from about −50 decismels to +60 decismels.

Suitable examples of chemosensory agents include one or more of the following compounds: trichloroethene, 1,2-dichloropropane, isobutyl isobutyrate, naphthalene, pyridine, 4-ethylphenol, phenylethyl methylethyl carbinol, tetrahydrothiophene, isovaleric acid, trimethylamine, L-carvone, pentadecalactone, 1-pyrroline, 1,8-cineole, isobutyraldehyde, 16-androsten-3-one, thiophane, PE-phenol, CA-phenone. Suitable gustatory chemosensory agents include salt (NaCl), sucrose, hydrochloric acid (HCl), urea, and phenylthiocarbamide (PTC). The preferred chemosensory agent is PE-phenol.

The kit can also optionally include a chart indicating the normal threshold concentration values for at least chemosensory agent. The threshold concentration of the chemosensory agent detected by the patient is compared to the normal or expected value on the chart. At least a 5 decismel change in the threshold level detected by the patient of a chemosensory agent can be identified and correlated with a psychiatric disorder or central or peripheral nerve dysfunction.

The kit also includes a chart correlating at least a 5 decismel change in the threshold detection of a chemosensory agent with a psychiatric disorder. The chart includes the following correlations between changes in threshold levels of the detection for chemosensory agents with psychiatric diagnoses: a decrease in the threshold detection level of PE-phenol with depression; an increase in the threshold detection level of thiophane detected in the right nostril and a decrease in the left nostril with obsessive-compulsive personality disorder; an increase in the threshold detection levels for CA-phenone, pyridine, salt, and sucrose with a dependent personality disorder; a decrease in the threshold detection level of salt and sucrose with anti-social personality disorder; an increase in the threshold detection level detected of CA-phenone with atypical personality disorder; an increase in the threshold detection levels detected for pyridine and CA-phenone with a passive-aggressive personality disorder; an increase in the threshold detection level for carbinol with a somatization disorder; and an increase in the threshold detection level of CA-phenone and thiophane with schizoid personality disorder.

The preferred kit contains 10 different concentrations of each of the following chemosensory agents: PE-phenol, thiophane, pyridine, CA-phenone, carbinol, salt, sucrose and phenothiocarbimide (PTC). The preferred kit also contains a chart showing the normal threshold concentration values for each of these chemosensory agents for each sex and age group and optionally indicating hyposmia, anosmia, and hyperosmia. The preferred kit also contains a chart, such as shown in Table V, correlating at least a 5 decismel change in the threshold level detected of a chemosensory agent with a psychiatric disorder.

EXAMPLE I

Forty-six consecutive patients presenting to the Smell and Taste Treatment and Research Foundation with chemosensory dysfunction were evaluated for olfactory and gustatory dysfunction as well as psychological dysfunction. The patients' mean age was 40 years with a slight majority being men (61%), n=28. Presenting chemosensory complaints include: hyposmia, hypogeusia 96% (44), dysgeusia 20% (9) and phantageusia 37% (17). These problems were associated with diverse etiologies, as shown in Table I.

TABLE I

| ETIOLOGY OF CHEMOSENSORY DISORDER (n = 46) | | |
|---|---|---|
| | Patients | Percentage |
| Post-Traumatic | 21 | 46% |
| Post-Infectious | 16 | 35% |
| Allergic Rhinitis | 12 | 26% |
| Polyposis | 6 | 13% |
| Medication-Induced | 2 | 4% |
| Other | 20 | 43% |

The patients underwent psychiatric and neurological histories and examinations. They completed extensive olfactory and gustatory tests including the Smell Identification Test™, unilateral threshold testing, including carbinol, PE phenol, PD lactone, cineole, thiophane, pyridine, and CA phenone, and the Accusens T™ Taste Test (see Table II).

TABLE II

| CHEMOSENSORY TESTS | | |
|---|---|---|
| Gustatory | Unilateral Olfactory Threshold Tests | Olfactory |
| NaCl | Carbinol | UPSIT - Formal |
| Sucrose | PD Lactone | Pennsylvania |
| HCl | Cineole | Olfactory Test |
| Urea | Thiophane | |
| PTC | Pyridine | |
| | CA Phenone | |

Written psychological testing including the Minnesota Multiphasic Personality Inventory II™ (MMPI-II), the Millon Clinical Multiaxial Inventory II™ (MCMI-II), and Beck Depression Inventory™.

The Smell Identification Test™ was obtained from Sensonics, Inc. of Haddenfield, N.J., and was conducted according to standard methodologies as described in the *Smell Identification Test™ Administration Manual*. Briefly, patients were tested for smell identification and sensitivity to 40 stimuli using scratch and sniff cards. Each subject rated the fragrance samples by scratching with a pencil included with the test cards, sniffing, and then identifying the odorant as one of four choices. A label could be repeatedly scratched as needed before moving to the next odorant and returning to previous odors was allowed.

The results of the patient's score on the Smell Identification Test™ were evaluated by reference to the established normal values for age and gender provided in the *Smell Identification Test*™ *Administration Manual* on pages 19 and 20. The patient's total number of correct responses (maximum of 40) was established by use of the test's scoring key. The patient's test score is located in the far left hand column of Table 1 for women and Table 2 for men. The age group is located along the top of the table and the subject's percentile score is read at the intersection of test score row and age group column. The percentile value reflects the percentage of normal patients having that score.

A diagnosis for an olfactory dysfunction is made by identifying whether the person's test score falls within the anosmia (total inability to perceive odor) or microsomia range (decreased smell ability). Generally, scores falling in the following ranges are indicative of smell dysfunction:

| Smell Identification Test Score | Olfactory Diagnosis |
| --- | --- |
| 0–5 | Probable malingering |
| 6–19 | Total anosmia |
| 20–33 | Microsomia (males only) |
| 20–34 | Microsomia (females only) |
| 34–40 | Normosmia (males only) |
| 35–40 | Normosmia (females only) |

The unilateral threshold test was conducted according to standard methods as described by J. Amoore et al., *Rhinology*, 21:49–54 (1983). Briefly, the patient's ability to detect increasing amounts of carbinol, PD-lactone, cineole, thiophane, pyridine, PE-phenol, and CA-phenone in the left and right nostrils was tested. The standards in decismels were obtained from OlfactoLabs, El Cerrito, Calif. For example, the threshold level of PE-phenol detected by a patient was determined by presenting the patient with 64 different bottles of different concentrations of PE-phenol. The patients were presented with bottles of different concentrations compared to the blank and asked to identify the bottle with the substance. The patient was presented with the bottles in random order and needed to correctly identify the substance three times in order to identify the patient's threshold concentration. The level at which the patients in the study detected each of the compounds was compared to known or expected values. The standard samples from OlfactoLabs were already calibrated in decismels. If the amount detected by the patient was lower than the expected values, the patient was more sensitive to the compound and detected the chemosensory agent at a negative decismel value. If the amount detected known was greater than the expected value, the patient was less sensitive to the compound and detected the chemosensory agent at a positive decismel value.

Odor thresholds are expressed on the "decismel scale". The mean threshold concentration of a chemosensory agent detected by a control group of 20-year olds is set at the 0 value. A decismel is calculated by dividing the concentration of the chemosensory agent detected by the patient to the normal threshold concentration (using the published value or empirically determining the value) and then taking the logarithm of the quotient. The logarithm of the quotient is then multiplied by 20 to obtain the decismel value. Decismel values can be positive or negative. A positive decismel value indicates the patient is less sensitive to the chemosensory agent, i.e. has a higher threshold detection concentration. A negative decismel value indicates that the patient is more sensitive to the compound, i.e. has a lower threshold detection concentration. An increase in the threshold concentration value over the mean threshold concentration value of two-fold corresponds to 6 decismels. The suggested thresholds for hyposmia are 30 ds and of functional anosmia at 54 ds. The normal mean threshold values for each chemosensory agent are known and can be used to convert the threshold concentration into decismels. A change of at least 5 ds from the expected value was considered a significant change in the threshold level of detection of the compound.

The Accusens T Test® was conducted according to standard methods as described by the *Accusens T*™ *Taste Function Kit Manual*. Briefly, the ability of the patients to taste sodium chloride (NaCl), sucrose, hydrochloric acid (HCl), urea, and phenylthiocarbamide (PTC) was evaluated by the patients tasting solutions containing increasing amounts of the compound.

The ability of the patients to detect and recognize the type and intensity of the solution was measured. Two drops of each of three solutions was placed on a patient's tongue successively. Two of three solutions were water and one of the solutions was either salty (NaCl), sweet (sucrose), sour (HCl) and bitter (PTC). Three different concentrations of salt, sucrose and HCl were tested. The PTC test was the last test performed. The patient was instructed to identify which one of the three solutions was different, whether it was salty, sweet, sour or bitter, and to estimate the degree of the taste on a scale of 1 to 100. All three judgments must be correct for diagnosis of normal taste. If the patient could not detect correctly the different tastant or recognize each tastant, the next higher concentration of the tastants was tested in the same manner until the patient correctly identified the tastants. The patient's responses were compared to established values for normal taste detection and recognition provided in the test kit. Any failure to detect or recognize the tastants is indicative that the patient has hypogeusia.

If the patient correctly detects and recognizes all of the tastants but gives intensity responses less than 5%, then a second test is done. Patients taste each of three different concentrations of the NaCl solution, sucrose solution and HCl solution and rate the intensity of each of the solutions. Responses considered normal for the lowest concentration are 5% to 15%, responses considered normal for the middle concentration are 10% to 30% and responses considered normal for the highest concentration are 25% to 50%. Any response lower than the lower percentage of the ranges noted above is abnormal and indicative of hypogeusia.

The patients also were evaluated for psychiatric disorders using the MMPI-II, the MCMI-II, and the Beck Depression Inventory. The MMPI-II is available from National Computer Systems and is administered according to standard methodologies as described in *Psychological Assessment with the MMPI*, A. Friedman et al., editor, Laurence Erlbaum Assoc., publishers (1989) at pages 40–53. The MMPI-II provides a basis for diagnosis of hypochondriasis, depression, anxiety disorder, passive-aggressive personality, psychosis, borderline personalities, schizoid disorder, paranoia, as described in *Psychological Assessment with the MMPI*, cited supra., at pages 150–198. The MCMI-II is available from National Computer Systems and is administered according to standard methods described in the *Test Administration Instruction Booklet*. The results from the MCMI-II provide a basis for diagnosis of DSMIIIR-Axis II diagnosis. The Beck Depression Inventory is administered according to standard methodologies as described in the *Test Administration Instruction Booklet*. The results from the Beck Depression Inventory provide a measure of the severity of the depression.

The MMPI-II and the MCMI-II provide a basis for a diagnosis of a DSMIII-R Axis I or DSMIII-R Axis II disorder. The DSMIII-R Axis I disorders include generalized anxiety disorder and a chronic form of depression known as dysthymia. The DSMIII-R Axis II disorders include obsessive-compulsive personality disorder, narcissistic personality disorder, personality disorder N.O.S.; histrionic personality disorder; dependent personality disorder; schizoid personality disorder; antisocial personality disorder; atypical personality disorder; passive-aggressive personality disorder; and somatization disorder. The symptoms and diagnosis of these psychological disorders are described in the American Psychiatric Association's *Diagnostic and Statistical Manual of Mental Disorders*, 3rd edition, Wash, D.C. (1987), which is hereby incorporated by reference. The Beck Depression Inventory measures energy loss, problems thinking, as well as other factors and provides a basis for determining the severity of a depression.

Diagnosis of the psychiatric disorder is made based upon the results of MMPI-II or MCMI-II tests and psychiatric interview. As shown in Table IV, some of the 46 patients were classified into more than Axis I or Axis II diagnosis.

The results from the olfactory and gustatory tests and psychological tests were analyzed statistically by standard methods, as described in *Applied Depression Analysis and Other Multivariant Methods*, and a correlation between the chemosensory test data and the diagnosis indicated by the psychological test data was conducted. The data were analyzed employing univariate methods for simple summary statistics and by applying correlation methods to examine statistical relationships among the study variables. Although the conventional level of significance ($p<0.05$) was initially used to select the groups of variables exhibiting significance, since there were multiple tests involved, the significance levels were further subjected to Bonferroni Correction as described by Kleinbaum et al., *Applied Digression Analysis and Other Multivariant Methods*, DWS Kent Publishing, Boston, Mass. (1988), and only those correlations meeting the Bonferroni criterion were reported as being significant.

The results shown in Tables III and IV indicate that patients exhibiting a chemosensory dysfunction also exhibited the symptoms of at least one and sometimes more than one psychiatric disorder. As defined by the results of the MMPI-II or MCMI-II, 33% (15) had a DSMIIIR axis I diagnosis; 96% (44) met a total of 74 DSMIIIR axis II diagnoses; and 4% (2) were felt to be psychiatrically normal and did not meet a DSMIIIR axis I or axis II diagnosis. (See Tables III and IV.)

TABLE III

| AXIS I DIAGNOSIS (n = 46) | | |
|---|---|---|
| | Patients | Percentage ± S.E.* |
| Generalized Anxiety Disorder | 10 | 22% ± 12 |
| Dysthymia | 9 | 20% ± 12 |
| Other Axis I Diagnoses | 11 | |
| Total number of Axis I Diagnoses = 30 Percentage of patients with at least one Axis I Diagnosis = 33% ± 14 | | |

*Standard Error of the percentage for 95% confidence interval.

TABLE IV

| AXIS II DIAGNOSIS (n = 46) | | |
|---|---|---|
| | Patients | Percentage ± S.E.* |
| Obsessive Compulsive P.D. | 16 | 35% ± 14 |
| Narcissistic P.D. | 10 | 22% ± 12 |
| Personality Disorder N.O.S. | 10 | 22% ± 12 |
| Histrionic P.D. | 9 | 20% ± 12 |
| Dependent P.D. | 8 | 17% ± 11 |
| Schizoid P.D. | 7 | 15% ± 10 |
| Other Axis I Diagnoses | 14 | |

*Standard Error of the percentage for 95% confidence interval.

The most frequent axis I diagnoses were generalized anxiety disorder 22% (n=10); dysthymia (9); and somatization disorder 11% (5) (Table III). The most frequent DSMIIIR axis II diagnoses were obsessive-compulsive personality disorder, 35% (n=16); narcissistic personality disorder, 22% (10); personality disorder not otherwise specified, 22% (10); and histrionic personality disorder, 20% (9). (See Table IV.)

In general, the greater perceived severity of the olfactory problem, the more likely the patient has an DSMIIIR axis II obsessive-compulsive personality disorder ($p<0.018$). This is predictable since the obsessive nature of this psychiatric disorder would tend to amplify any unexpected somatic complaints. Eighty percent of subjects had chemosensory complaints for less than 7 years. Longer duration of chemosensory complaints is correlated to DSMIIIR axis II abnormalities including avoidant personality disorder ($p<0.001$), passive-aggressive personality disorder ($p<0.007$), and borderline personality disorder ($p<0.001$), as well as DSMIIIR axis I schizophrenic disorders ($p<0.01$) and paranoid disorders ($p<0.001$). The longer the chemosensory complaints persist, the more likely there is a co-existing DSMIIIR axis I major depression ($p<0.001$). This is further suggested by the correlation of increase in levels ($p<0.008$). The longer the problem exists, the worse the depression as measured by the Beck Depression Inventory ($p<0.001$).

In male subjects, the correlation between major depression ($p<0.0005$), energy loss ($p<0.003$), and problems thinking ($p<0.002$) was especially prominent. As duration of chemosensory symptoms lengthens, other psychiatric disorders appear in men including axis I diagnosis of schizophrenia ($p<0.009$), axis II diagnoses of avoidant personality disorder ($p<0.0005$), borderline personality disorder ($p<0.0005$), and passive-aggressive personality disorder ($p<0.007$).

TABLE V

| | Depression (Beck Inv.) | Obsessive-Compulsive | Dependent | Anti-Social | Atypical | Passive Agressive | Soma-tization | Schizotypal |
|---|---|---|---|---|---|---|---|---|
| PTC | | | (unable)* p<.007 | | | | | |
| PE-Phenol | | | | | | | | |
| Right | ↓ p<.016* | ↓ p<.008* | | | | | | |
| Left | ↓ p<.007 | | | | | | | |
| UPSIT | | | | | | | ↓ p<.02** | |
| Thiophane | | | | | | | | |
| Right | | ↑ p<.0005* ↑ p<.006 | | | | | | ↑ p<.006 |
| Left | | ↓ p<.009 | | | | | | |
| Pyridine | | | | | | | | |
| Right | | | | | | ↑ p<.01 | | |
| Left | | ↑ p<.011* | | | | ↑ p<.008 | | |
| Ca-Phenone | | | | | | | | |
| Right | | ↑ p<.007* | | ↑ p<.001 | ↑ p<.001 | | ↑ p<.001 | |
| Left | | | | ↑ p<.001 | ↑ p<.001 | | ↑ p<.001 | |
| Carbinol | | | | | | | | |
| Right | | | | | | | ↑ p<.008 | |
| Left | | | | | | | ↑ p<.001 | |
| Salt Taste | | | H p<.007 | Hy p<.01 | | | | |
| Sucrose Taste | | | H p<.017* | Hy p<.01 | | | | |

*Females only
**Males only
At least a 5 decismel decrease in the threshold amount detected from the normal value for same age group and gender
At least a 5 decismel increase in the threshold amount detected from the normal value for same age group and gender.
H = Hypogeusia
HY = Hypergeusia The results in Table V also show that changes in specific chemosensory sensitivities correlate with diagnoses of psychiatric disorders. Depression and the severity of depression correlates with at least a 5 decismel decrease in the threshold level of detection of PE phenol in the left nostril and also in the right nostril in women. Patients diagnosed with an obsessive-compulsive disorder show at least a 5 decismel (about 2-fold) increase in the threshold sensitivity for thiophane in the right nostril and at least a 5 decismel (about 2-fold) decrease in the threshold level detected in the left nostril. Women diagnosed with the obsessive-compulsive disorder also show a decrease in the threshold level of PE phenol detected in the right nostril. Women diagnosed with dependent personality disorder show at least a 5 decismel (about 2-fold) increase in the threshold level of detection of pyridine in the left nostril and an increase in the threshold level detected of CA phenone in the right nostril, as well as a hypogeusia for tasting sucrose and an inability to detect PTC. Both men and women diagnosed with dependent personality disorder show an increase in the threshold taste level for salt. Patients diagnosed with antisocial personality disorder show a decreased threshold taste level for salt and sucrose. Patients diagnosed with atypical personality disorder show at least 5 decismel increase in the threshold level for CA phenone. Patients diagnosed with passive-aggressive personality disorder show at least 5 decismel increase in the threshold detection level for pyridine and CA phenone. Patients diagnosed with a somatization disorder show at least 5 decismel increase in the threshold level of detection of carbinol and a decrease in male patients of the UPSIT score. Patients diagnosed with a schizoid personality disorder show increase in the threshold detection levels for CA phenone and thiophane. Thus, patients presenting with a specific chemosensory dysfunction can also be diagnosed for a psychiatric dysfunction using the chemosensory assays.

The results confirm a high incidence of mood disorders and extensive chemosensory testing procedures allow detection of additional psychiatric diagnoses not previously reported to co-exist with chemosensory complaints. The recognition of this co-morbidity is important for clinicians for the proper diagnosis and treatment of patients with chemosensory disorders.

All patents and publications cited herein are hereby incorporated by reference. While the present invention has been described in connection with the preferred embodiment thereof, it will be understood many modifications will be readily apparent to those skilled in the art, and this application is intended to cover any adaptations or variations thereof. It is manifestly intended this invention be limited only by the claims and equivalents thereof.

What is claimed is:

1. A method of diagnosing a somatization disorder in a patient having a chemosensory dysfunction, comprising:

administering a plurality of concentrations of 3-methyl-5-phenyl-3-pentanol to the patient to determine the patient's threshold detection level for 3-methyl-5-phenyl-3-pentanol;

comparing the threshold detection level of the patient with a standard threshold amount for 3-methyl-5-phenyl-3-pentanol detected by a normal person of the same sex and age as the patient;

identifying at least a 5 decismel increase in the threshold detection level of the patient compared to the standard threshold amount for 3-methyl-5-phenyl-3-pentanol; and correlating the at least 5 decismel increase in the threshold detection level with a diagnosis of somatization disorder in the patient.

2. A method for confirming a somatization disorder in a patient, comprising:

administering a plurality of concentrations of 3-methyl-5-phenyl-3-pentanol to the patient to determine the patient's threshold detection level for 3-methyl-5-phenyl-3-pentanol;

identifying at least a 5 decismel increase in the threshold detection level of the patient compared to the standard threshold amount for 3-methyl-5-phenyl-3-pentanol; and correlating the at least 5 decismel increase in the threshold detection level with a diagnosis of somatization disorder in the patient; and administering a standard written psychological test diagnostic for somatization disorder to confirm the diagnosis of somatization disorder in the patient by the 3-methyl-5-phenyl-3-pentanol test.

* * * * *